United States Patent [19]
Yamamoto

[11] Patent Number: 5,610,993
[45] Date of Patent: Mar. 11, 1997

[54] METHOD OF CO-CENTERING TWO IMAGES USING HISTOGRAMS OF DENSITY CHANGE

[75] Inventor: Makoto Yamamoto, Tokyo, Japan

[73] Assignee: Yozan Inc., Tokyo, Japan

[21] Appl. No.: 989,501

[22] Filed: Dec. 10, 1992

Related U.S. Application Data

[63] Continuation of Ser. No. 727,957, Jul. 10, 1991, abandoned.

[30] Foreign Application Priority Data

Jul. 12, 1990 [JP] Japan .................................. 2-184777

[51] Int. Cl.$^6$ .................................................... G06K 9/00
[52] U.S. Cl. ........................... 382/124; 382/168; 382/294
[58] Field of Search .................................. 382/4, 18, 45, 382/124, 168, 170, 294; 356/71

[56] References Cited

U.S. PATENT DOCUMENTS

| | | | |
|---|---|---|---|
| 4,607,384 | 8/1986 | Brooks | 382/4 |
| 4,827,527 | 5/1989 | Morita et al. | 382/4 |
| 5,040,224 | 8/1991 | Hara | 382/4 |

FOREIGN PATENT DOCUMENTS

| | | | |
|---|---|---|---|
| 0173972 | 3/1986 | European Pat. Off. | |
| 61-100 | 1/1986 | Japan | A61B 5/10 |
| 61-101 | 1/1986 | Japan | A61B 5/10 |
| 61-28171 | 2/1986 | Japan | G06K 9/00 |
| 61-145686 | 7/1986 | Japan | G06K 9/00 |
| 87/06378 | 10/1987 | WIPO | 382/4 |
| 62-266686 | 11/1987 | Japan | G06K 9/00 |

OTHER PUBLICATIONS

Matsuura et al., "A Method for Fingerprint Image Enhancement Using the Ridge Direction", The Transactions of the Institute of Electronics, Information and Communication Engineers, D–II, vol. J72–D–II, No. 2, pp. 302–306, Feb. 1989.

Sasakawa et al., "Personal Verification System With High Tolerance of Poor Quality Fingerprints", The Transactions of the Institute of Electronics, Information and Communication Engineers, D–II, vol. J72–D–II, No. 5, pp. 707–714, May 1989.

Asai et al. "Automated Fingerprint Identification by Minutia–Network Feature—Matching Processes–", The Transactions of the Institute of Electronics, Information and Communication Engineers, D–II, vol. J72–D–II, No. 5, pp. 733–740, May 1989.

Asai et al., "Automated Fingerprint Identification by Minutia–Network Feature—Feature Extraction Process–", The Transactions of the Institute of Electronics, Information and Communication Engineers, D–II, vol. J72–D–II, No. 5, pp. 724–732, May 1989.

"Algorithm of Fingerprint Verification System", Nikkei Electronics, Jan. 9, 1989 (No. 464).

*Primary Examiner*—Leo Boudreau
*Assistant Examiner*—Andrew W. Johns
*Attorney, Agent, or Firm*—Cushman, Darby & Cushman

[57] ABSTRACT

An image positioning method for co-centering two images including ridges with each other, first a density value of each pixel of an image to be examined and a reference image are calculated. A change of density value between pixels in neighborhoods along the first and the second directions of each pixel of the image to be examined and the reference image are determined and a histogram of density change along the first and second directions of the image to be examined and the reference image is also determined. A maximum or minimum point of the histogram of the first and second directions is determined as a characteristic point of the image to be examined and the reference image. The image to be examined and the reference image are determined to fit when the characteristic points coincide with each other.

4 Claims, 5 Drawing Sheets

METHOD OF CO-CENTERING TWO IMAGES USING HISTOGRAMS OF DENSITY CHANGE

This is a continuation of application Ser. No. 07/727,957, filed on Jul. 10, 1991, which was abandoned upon the filing hereof.

FIELD OF THE INVENTION

The present invention relates to a method for fitting an image location including ridges, applied to a fingerprint verification system, for example.

BACKGROUND OF THE INVENTION

A conventional fingerprint verification method adopted the characteristics of branch points, end points and curvature as parameters for comparison. Image binarization and thinning with centering were prerequisites for this comparison. The positioning of the sample image and the master image were also prerequisites so that corresponding points of the two images fit each other. In the conventional method, the characteristic points in both images were considered the standards and it was necessary to extract the characteristics clearly. Therefore conventionally, verification accuracy was poor because of the bad quality of an image, that is, a pinched part or a broken part of the ridge, or noise. That is to say, the conventional fingerprint verification was easily influenced by micro data of characteristics and the condition was strict for inputting the image.

SUMMARY OF THE INVENTION

The present invention is invented so as to solve the above problem and has an object to provide an image positioning method for images including ridges, which can ease the restriction, for input of the sample image.

An image positioning method according to the present invention is characterized in the following steps.

i) Calculating a density value of each pixel in an image to be examined and a reference image; ii) calculating a change of density values between pixels in neighborhood along the first and the second directions of each pixel of the image to be examined and the reference image; iii) calculating a histogram of density change along the first and second directions of the image to be examined and the reference image; iv) defining the maximum or minimum point of histogram of the first and second directions to be characteristic point, the image to be examined and the reference image are to be fit so as to the characteristics point coincide each other.

This image positioning of the present invention is minimally influenced by micro characteristics because an inputted image is processed as an image in gray-level and fitted based on macro point of view.

DETAILED DESCRIPTION OF THE PREFERRED EMBODIMENTS

Hereinafter, an image comparison method relates to the present invention is described with referring to the attached drawn embodiments.

Figure 2:
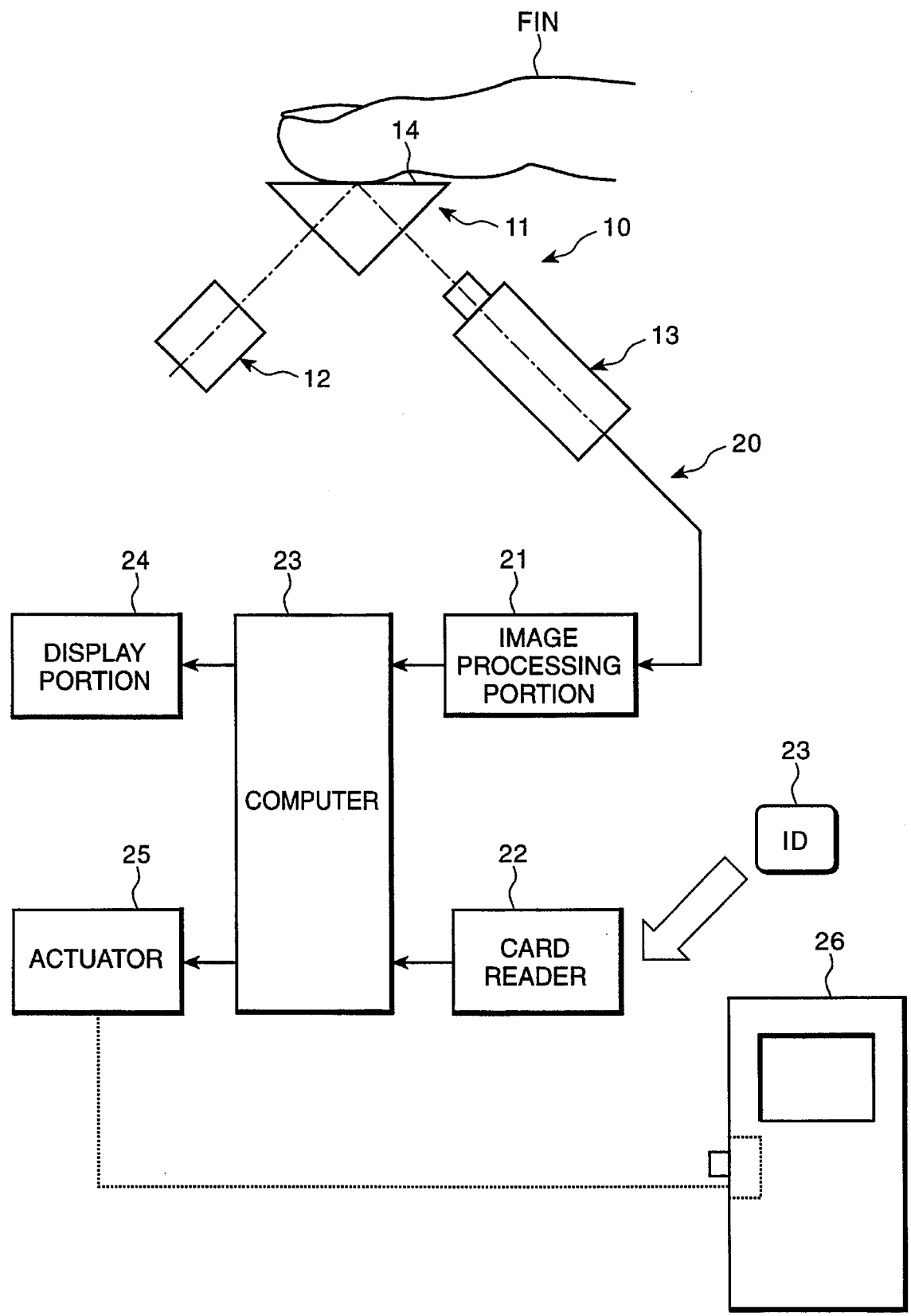
FIG. 2 shows the block diagram to show a fingerprint verification system.

FIG. 2 shows a fingerprint verification system using the image comparison method of the present invention. The fingerprint verification system comprises image input system 10 and comparison system 20: the image photographed in image input system 10 is compared in comparison system 20. Image inputting system 10 provides incident light on right angled prism 11 from light source 12, and detects all reflected light by CCD camera 13. Slope 14 of prism 12 is the detecting surface. FIN of a finger to be detected fingerprint is touched to slope 14. When a finger FIN is not touched, all light is reflected and white image is detected by CCD camera 13.

Figure 3:
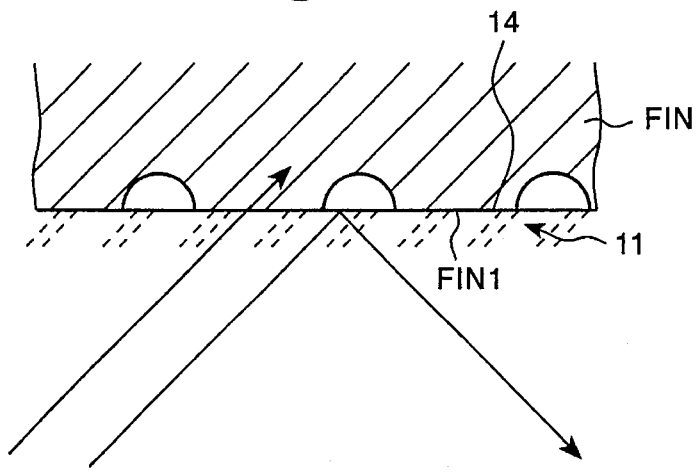
FIG. 3 shows the diagram of the part touched a finger on the slope of right prism with enlargement.

As FIG. 3, since the refractive index of the surface of the prism is changed on the surface touched by a finger FIN 1 (the ridges of a fingerprint), the light goes through the surface without refraction. Therefore, the ridges of the fingerprint are inputted to the CCD camera as dark lines.

Comparison system 20 comprises image processing portion 21 and card reader 22. Inserting ID card 23 into card reader 22 by the one to be examined, master data is read out and the data inputted from image inputting system 10 is compared with the master data. The comparison is executed in computer 23. The comparison result is indicated on display portion 24 and simultaneously, an object door 26 is unlocked by the working of actuator 25 when it is found that the two fingerprints correspond to each other by the comparison.

Various ways can be adopted for the specification of master data, such as input of ID number from keyboard by the one to be examined.

Figure 4:
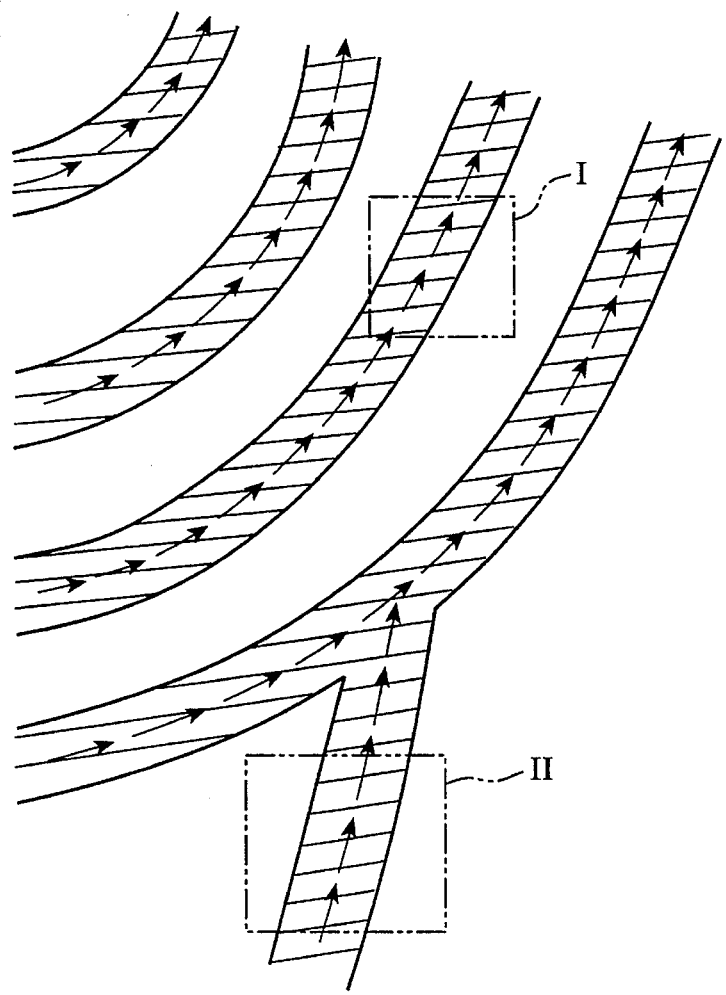
FIG. 4 shows an example of ridges of a fingerprint.
Figure 5A:
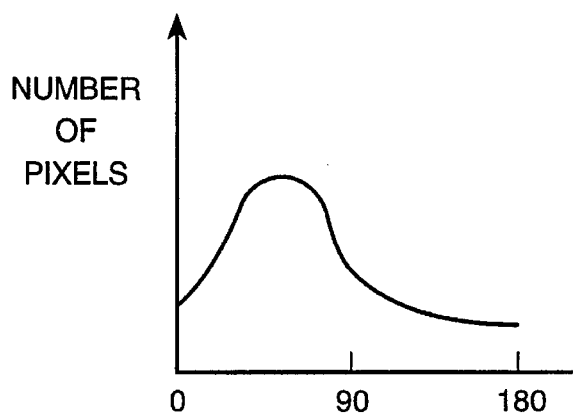
FIG. 5(A) shows a histogram concerning to the density change of pixels in area "I" in FIG. 4.
Figure 5B:
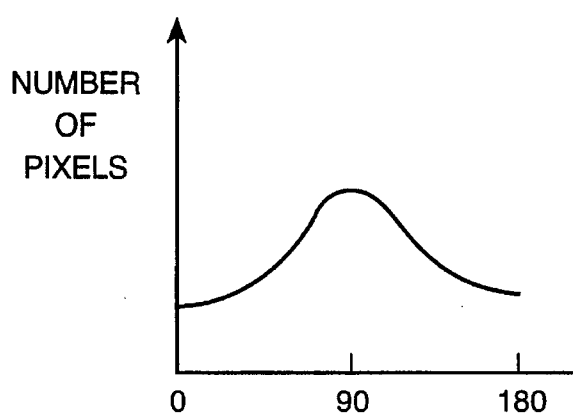
FIG. 5(B) shows a histogram concerning to the density change of pixels in area "II" in FIG. 4.

FIG. 4 shows general directions of ridges of a fingerprint by arrows. The inventors have adopted the histogram in the direction with minimal partial differential of density value on each pixel as the index to show the general direction. For example, as density values change for each pixel included in area I inclines to be minimum in the direction rotated 45° counterclockwise from the horizontal direction, the partial differential value of the density of each pixel in the area has a high frequency which is minimum in the direction of 45°. Therefore, the histogram in FIG. 5(A) can be obtained concerning the change of density value of pixels in area I. On the other hand, as the change of density value of each pixels included in area II inclines to be minimum in the direction rotated 90° counterclockwise from the horizontal direction, the partial differential value of the density of each pixel in the area has high frequency which is minimum in the direction of 90°. The histogram in FIG. 5(B) can be obtained concerning to the change of density value of pixels in area II.

The following processings are executed to obtain such histograms.

First, a density value is calculated for each of the pixels in the sample image of inputted fingerprint image. The density value is calculated for each pixel and stored in the memory of computer 23 for a master image of fingerprint image, to be used as the standard for comparing with the sample image.

Figure 6:
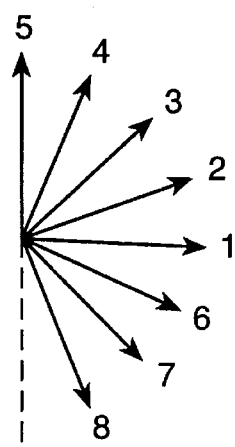
FIG. 6 is a diagram to show the direction of partial differential.

Next, a partial differential value of a density between adjacent pixels is calculated for each pixel. Here, an adjacent pixel designates not only pixels which are just next to one another but also pixels that are distant from one another by up to a few pixels. Partial differential is performed with the range of 157.5° as shown in FIG. 6, concerning to horizontal direction (number 1), the directions rotated 22.5° counterclockwise in sequence from horizontal direction (numbers 2, 3, 4 and 5) and the directions rotated 22.5° clockwise in sequence from horizontal direction (numbers 6, 7 and 8). Setting X-coordinate in the horizontal direction and Y-coordinate in perpendicular direction, and assuming the change quantity of density to be Δd, "z" performed partial differential is calculated as below.

$$Z = \frac{\Delta d}{\Delta x + \Delta y}$$

Partial differential in digital image is scattering: especially concerning to the distance element, some necessities to adopt a rather large distance occurs according to the direction of partial differential. However when the distance becomes too large, a differential is performed between a ridge and another ridge beyond a trough and the fingerprint ridge characteristics is lost. Therefore a small value should be used as the distance value, while the direction precision is enhanced as much as possible. Image input system 10 in FIG. 2 needs amendment for elements in Y direction in the image to be inputted to the CCD camera 13 in order to observe the fingerprint from the slant direction of 45°. Good results are obtained by using distances of 0° (Δx=2, Δy=0), 22.5° (ΔX=2, Δy=1), 45° (ΔX=2, Δy=2) and 67.5° (ΔX=2, Δy=3) as the distances of partial differential considering the amendment.

When calculating the value through partial differentials in the directions from the number 1 to 8 in FIG. 6 of each pixel, the smaller one is inputted to memory, comparing the partial differential value already calculated and newly calculated. Therefore, the minimal partial differential value is stored in the memory when the calculations in 8 directions are completed by inputting the smaller one to memory while performing partial differential in each direction. The minimal differential value in all the pixels is calculated by performing the processing for all the pixels.

Next, calculating partial differential in each direction from the number 1 to 8 of each pixel, the partial differential values are compared with the minimal one already calculated. When the newly calculated partial differential value calculated corresponds to the minimal one, the number corresponding to the "direction" of the partial differential value then (the numbers from 1 to 8 in FIG. 6) is stored in the memory in image processing portion. Consequently, the direction with the minimal partial differential value is calculated for all the pixels, and the distribution of directions with the minimal partial differential value is obtained for the whole image. In this way, the information of the original image can be used in maxim as direction elements in every part of image are extracted directly from a gray-level image.

When the distribution of directions with the minimal partial difference value is obtained in a sample image, it is possible to determine the tendency of fingerprint ridges. Fingerprint verification can be performed by comparing the distribution with a master image. That is, by putting direction data of the minimal partial differential obtained in every pixel between sample image and master image, the data is compared with every corresponding image. In the present embodiment, as described later, dividing an image into plural blocks and calculating an index according to the direction of the minimal value, the sample image is compared with the master image using the index. The way is adopted to compare sample image and master image over a wide view.

The fingerprint comparison can be executed in every image, not by dividing it into blocks. That is, the sample image can be determined to correspond to the master image each other when 80% or more of the pixels correspond in the direction above.

Before the comparison between the sample image and the master image, fitting of these image locations is performed. The image positioning is explained referring to FIG. 1.

Figure 1:
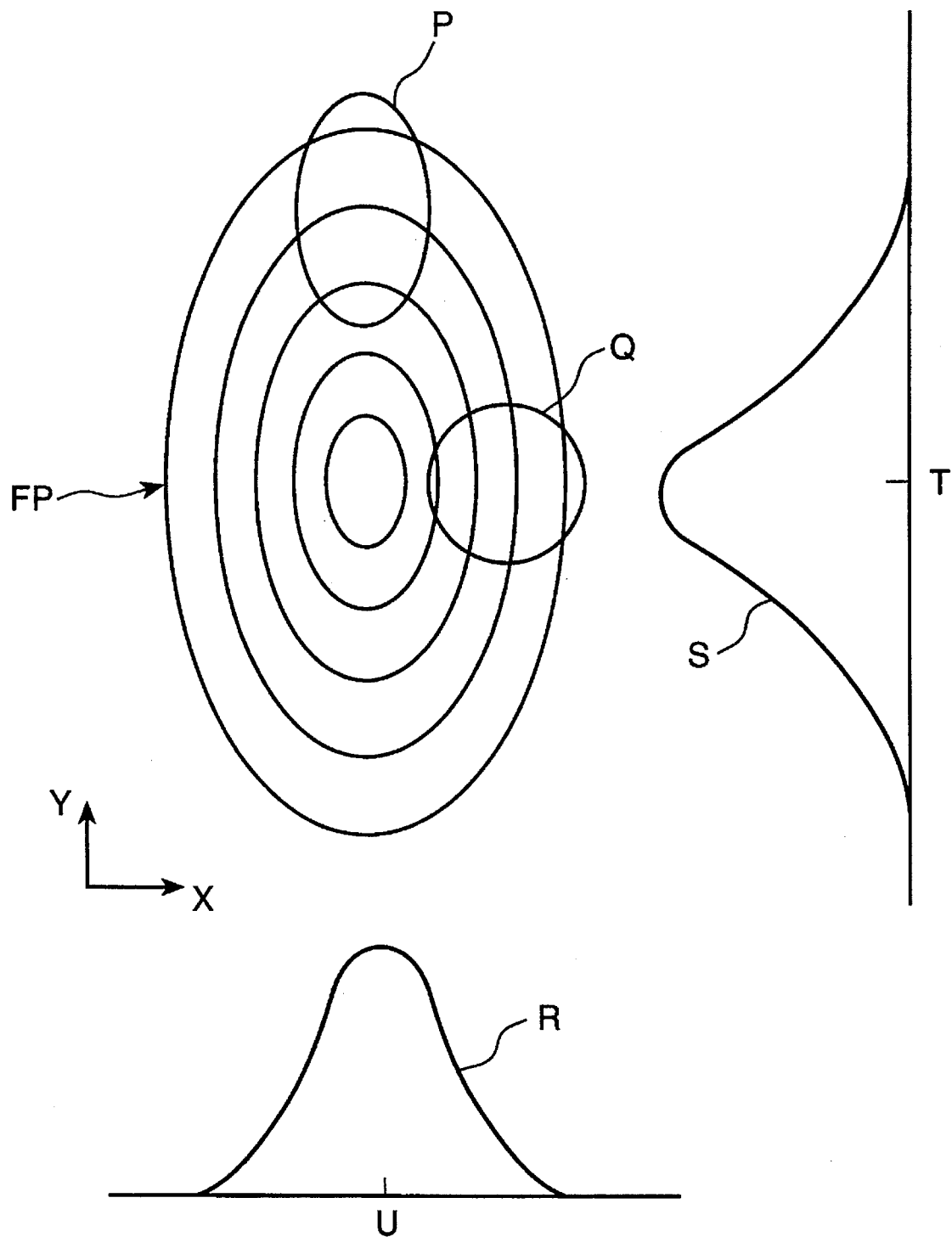
FIG. 1 shows the diagram for explaining an image positioning method relates to the present invention.

In FIG. 1, fingerprint ridge FP shows spiral, and pixels with the same density are along the spiral. Here, the horizontal direction and the vertical direction are defined as the X-direction and Y-direction, respectively. When a partial differential is performed on the quantity of change between adjacent pixels in direction and the change ratio of density value in the Y-direction is calculated, the change ratio is large in the part in which the ridge spreads in X-direction as the part of "P" and it is small in the part in which the ridge spreads in Y-direction as the part of "Q". Therefore, the partial differential value of density in the Y-direction has the histogram with the maximum on the center point, as shown with "R". In the same way, when the change ratio of density value is calculated in X-direction, it is small in the part in which the ridge spreads in the X-direction as the part of "P" and it is large in the part in which the ridge spreads in the Y-direction as the part of "Q". Therefore, the partial differential value of density in X-direction has the histogram with the maximum on the center point, as shown with "S".

In the present embodiment, the point of maximum ("T") of the histogram relates to the density change along X-direction ("S") is defined to be Y-coordinate of the center point of the image, and the point of maximum ("U") of the histogram relates to the density change along Y-direction is defined to be X-coordinate. The center point obtained in this way does not coincide with that of the configuration, but that of the characteristics of the image ("characteristics point", hereinafter)

When positioning the sample image and the master image, the characteristics point needs to be overlap with the predetermined acceptable difference. The way to deal with the predetermined acceptable difference is as follows. Parting the sample image and the master image into the subblocks in FIG. 7, the subblocks including characteristics points of both images are overlapped by the areas with 16×16 pixels. The coordinates of characteristics points may have measurement error and this would cause the characteristic points not to overlap between the master image and the sample image as the same one of the master image. When such a case occurs, the next processing is performed. When the sample image and the master image do not coincide after the identification evaluation, the identification ratio is evaluated again by shifting the area of 16×16 pixels by one pixel in the directions of up, down, right and left. On reevaluation, the master and the sample images are recognized to be identical when the identification ratio exceeds the predetermined value, on the other hand, the sample image is not recognized to be identical to the master image when the identification ratio does not satisfy the predetermined value by the shift of all directions—it is the final judgment.

Figure 7:
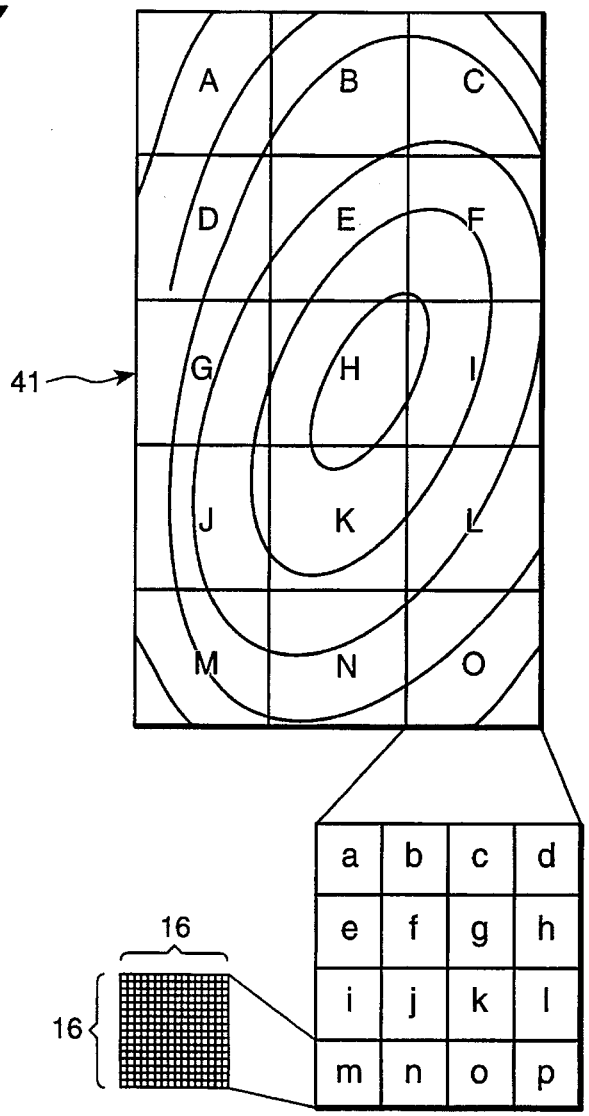
FIG. 7 is a diagram to explain the method to divide fingerprint image into blocks.

FIG. 7 shows the way to divide fingerprint 41 into blocks. Image 41 is divided into 15 blocks of A to O, which are divided into 16 subblocks of "a" to "p" each comprised of 16×16 pixels. In the present embodiment, calculating characteristics value according to the formula below, the sample image is compared with the master image.

Total variance is calculated in each of the subblocks of "a" to "p". It is defined by the following formula.

Total Variance = Variance between Classes +

$$\text{Variance within Classes} = \sin^2(\Theta/2) + (Vm + Vs)/2$$

In the formula above, $\Theta$ is the angle of direction lags to be the minimal values of partial differential of master image and sample image in each subblock: Vm is variance within classes in class in each subblock of master image: Vs is variance between classes in each subblock of sample image. In the present embodiment, total variance RE is defined as what is subtracted total variance defined by the formula above from 1. That is, total variance RE is defined by the formula below.

$$RE = 1 - \frac{\sin^2(\Theta/2) - (Vm + Vs)/2}{\cos^2(\Theta/2) - (Vm + Vs)/2} \qquad (1)$$

Total variance inclines to increase as higher coincidence.

Figure 8:
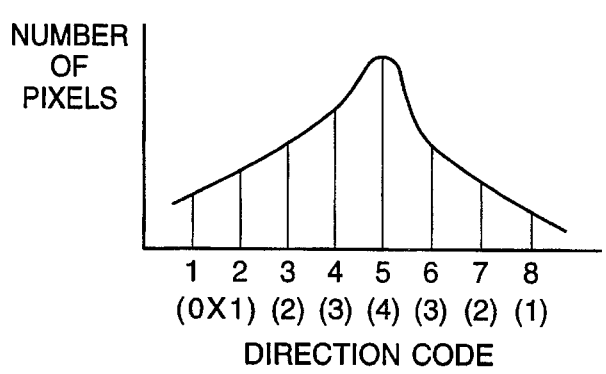
FIG. 8 shows a histogram of pixels corresponding to direction codes.
Figure 9:
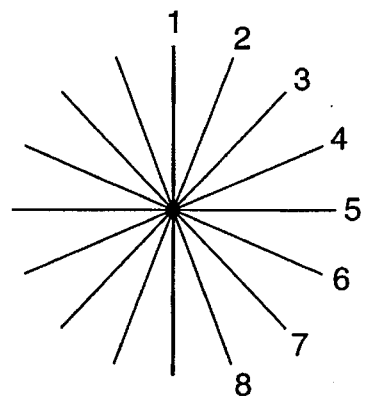
FIG. 9 is a diagram to show the definition of direction codes.

Variance within classes Vm and Vs in the master image and the sample image are calculated in order to calculate total variance defined by formula (1). It is described seeing FIG. 8 and FIG. 9. FIG. 8 shows the histogram of the number of pixels on direction codes and FIG. 9 shows the definition of direction codes: defining the direction code in perpendicular upper direction to be "1", it increases up to "8" as the direction rotates 22.5° clockwise from "1".

Determining the direction code "1" to be a provisional center point, a direction lag is calculated in comparison with direction code "1". The direction lags include 1, 2, 3, 4, 3, 2 and 1 on direction codes "2", "3", "4", "5", "6", "7", and "8", respectively (shown in parentheses in FIG. 8). As there is no consideration of direction lag of clockwise or counterclockwise, direction lags are the same in direction codes "2" and "8", "3" and "7" and "4" and "6".

Multiplying the weight by the number of pixels in each direction code corresponding to the direction lag, the sum total T is calculated. Here, assuming the angle of direction lag to be $\Theta$ the weight is $\sin^2\Theta$: the weight is 0.0 in the case of no direction lag, it is 0.15 in the case of 1 of direction lag, it is 0.5 in the case of 2 of direction lag, it is 0.85 in the case of 3 of direction lag, it is 1.0 in the case of 4 of direction lag. The reason why weight is multiplied to the number of pixels in each direction code is that pixel influence on variance within classes is supposed to become strong as further distant from provisional center point.

Variance within classes is calculated by dividing total sum T obtained in this way by 256 of the number of pixels in the subblock. The variance within classes is calculated assuming all direction codes to be provisional center points: that is, 8 of variance within classes are obtained for each subblock. Next, finding the minimal value in these variances within classes, it is provided to be the variance in classes in the subblock. And, the direction code corresponding to the minimal variance in classes is the one in the subblock. Consequently, variances within classes and direction codes can be obtained in each subblocks from "a" to "p".

Next, calculating the mean value of variance within classes in subblocks from "a" to "p", it is provided to be variance within classes in corresponding blocks from A to O. The variance within classes obtained in this way is Vm and Vs in the master image and sample image to be used in formula (1) above. In the same way, calculating the mean value of direction codes in subblocks from "a" to "p", provide it to be the direction code of corresponding blocks from A to O. The direction code is the one to be used in formula (1) above.

$\cos^2(\Theta/2)$ in formula (1) above of direction lag is calculated next. It is calculated through the process of: calculating the difference of direction codes between master image and sample image in every block, providing the angle corresponding to the difference to be $\Theta$. For example, when the difference between direction codes of master and sample image is 1, direction lag is 0.96 for $\Theta$ is 22.5°. In the same way, when the difference is 2, direction lag is 0.85 for $\Theta$ is 45° when the difference is 3, direction lag is 0.69 for $\Theta$ is 67.5°: when the difference is 4, direction lag is 0.5 for $\Theta$ is 90°.

Using direction lags (variance between classes) and variance within classes Vm and Vs obtained as above, total variance RE can be calculated in every block A to O through formula (1). Total variance RE changes from 0 to 1: as sample image resembles to master image, it is close to 1. For example, when sample image almost corresponds to master image, total variance RE is equal to or more then 0.8 in all blocks from A to O. On the other hand, when sample image does not correspond to master image, total variance RE is less then 0.7 in most blocks from A to O. When sample image almost corresponds but partially does not to master image, total variance RE is equal to or more than 0.8 in almost all the blocks but it is less than 0.7 in a part of the blocks.

Correlation is calculated next. It is defined as the following formula.

$$COR = \frac{\sum_{i=1}^{8} x(\Theta i) \times X(\Theta i)}{\sqrt{\sum_{i=1}^{8} x^2(\Theta i) \times \sum_{i=1}^{8} X^2(\Theta i)}} \qquad (2)$$

Where, COR is correlation, $x(\Theta i)$ is number of pixels in $\Theta i(\deg)$ direction in master image.

In the correlation, calculating it in every subblock from "a" to "p", its mean value is the correlation of corresponding block in the same way of the case of total variance. The correlation changes from 0 to 1: as a sample image resemble to the master image, it becomes close to 1.

Distance between classes is calculated in every block from A to O. The distance between classes is defined by the following formula.

$$DG = \frac{\sum_{i=1}^{8} \{x(\Theta i) - X(\Theta i)\}^2}{\sum_{i=1}^{8} x(\Theta i) \times \sum_{i=1}^{8} X} \qquad (3)$$

Where, DG is distance between classes, $x(\Theta i)$ is the number of pixels in sample image in the direction of $\Theta i(\deg)$.

Distance between classes is calculated in each subblock from "a" to "p", and their mean value is the distance between classes corresponding block, as in the same way of total variance and correlation. Distance between classes changes from 0 to 1: as a sample image resembles to the master image, it becomes close to 0.

As above, total variance, correlation and distance between classes are calculated in every block from A to O as to master image and sample image. For a judgment of substantial correspondence between master image and sample image, it is necessary total variance to be equal to or more than 0.7, correlation to be equal to or more than 0.96 and distance between classes to be equal to or less than 0.1. In other words, when even one block is out of these limits, the sample image is judged to be different from the master image.

As mentioned above, when a sample image is recognized to be different from the master image, it is compared with the master one in the same method above by shifting the relative location of the sample and the master images in horizontal direction by one subblock (from "a" to "p" in FIG. 7). When these images are recognized to be different from each other from the comparison, they are compared with in the same method by shifting the relative location in another direction by one subblock. When these images are recognized to be different from each other from the comparison by shifting the relative location in horizontal direction, the next comparison is executed by shifting the sample and the master images by one subblock in vertical direction relatively from the first locations.

Up to here, a sample image is compared with a master image by overlapping their center points with each other. When these images are recognized to be different from each other, the same comparison is performed by shifting one image by one subblock in the horizontal direction and shifting another image by one subblock in vertical direction from the first center location. The comparison of two images are performed five times in maxim by shifting them in horizontal direction and vertical direction. When they are recognized to be different from each other in all of five times, the sample image is judged to have no identification with the master image.

When such comparison method is adopted in fingerprint verification system as in FIG. 2, the door 26 is unlocked on the judgment of correspondence between a fingerprint to be examined (sample image) and a reference fingerprint (master image). When a fingerprint to be examined is not judged to correspond, the person to be examined is required to input again his fingerprint, or the message to reject going in is displayed without releasing the lock.

A fingerprint is not always within the range of all the block from A to O: for example on a corner block, there is a possibility for pixel data in subblocks from "a" to "p" is less then 256 (16×16 pixels). In such a case, total variance, correlation and distance between classes are to be calculated ignoring the pixel data in the subblock. When the ratio of invalid blocks is more than a certain value, the person to be examined is immediately required to input again his fingerprint. t is not necessary to use all the indexes of total variance, correlation and distance between classes: only one or two of them may be used for a comparison of images.

As mentioned above, the present invention can prevent the influence of the condition of an image in the minimum because a gray-level image is performed processing as it is and the location is fit based on the general view of characteristics of histogram of density change in the first and second directions.

What is claimed is:

1. An image positioning method for co-centering and verifying two images including ridges with each other, comprising the steps of:

receiving an input image portion to be examined corresponding to a fingerprint;

processing pixels of said input image portion to be examined, by:
calculating a density value of each pixel of said image portion to be examined;
calculating changes of density value, along first and second directions, between pixels of said image portion to be examined which have a predetermined distance therebetween;
using said changes in density value to obtain a histogram of density change along said first and second directions of said image portion to be examined; and
defining a maximum rate-of-change point of each said histogram along said first and second directions, respectively, as characteristic points of the image portion to be examined;

processing pixels of a reference image portion to be examined, by:
calculating a density value of each pixel of said reference image portion;
calculating changes of density value, along said first and second directions, between pixels of said reference image portion which have said predetermined distance therebetween;
using said changes in density value to obtain a histogram of density change along said first and second directions of said reference image portion; and
defining a maximum rate-of-change point of each said histogram along said first and second directions, respectively, as characteristic points of the reference image portion;

moving said image portion to be examined relative to said reference image until said characteristic points of said reference image portion and image portion to be examined coincide with each other, to co-center the images;

recognizing said image portions as co-centered when said characteristic points coincide with each other;

comparing said histograms of said image portion and said reference image portion with each other;

recognizing said image portions as matching when said histograms correspond to each other within a predetermined amount; and outputting a verification signal when said histograms correspond to each other within a predetermined amount wherein said calculating changes in density value step for said image portion and said reference image portion includes the steps of:

determining partial differentials of density data for each said density value;

determining minimal partial differential of density data from said partial differentials for each said density value; and determining said first and second directions according to said minimal partial differentials.

2. A method as in claim 1 wherein said partial differential values are calculated for each of a range of directions.

3. A method as in claim 1 wherein said density change is calculated as $$Z = \frac{\Delta d}{\Delta x + \Delta y}$$

where change quantity of density is $\Delta d$, the partial differential is $Z$, and $\Delta x$ and $\Delta y$ are changes in x and y coordinates respectively.

4. An image positioning method for co-centering and verifying two images including ridges with each other, comprising the steps of:

receiving an input image portion to be examined corresponding to a fingerprint;

processing pixels of said input image portion to be examined, by:

calculating a density value of each pixel of said image portion to be examined;

calculating changes of density value, along first and second directions, between pixels of said image portion to be examined which have a predetermined distance therebetween;

using said changes in density value to obtain a histogram of density change along said first and second directions of said image portion to be examined; and defining a maximum rate-of-change point of each said histogram along said first and second directions, respectively, as characteristic points of the image portion to be examined;

processing pixels of a reference image portion to be examined, by:

calculating a density value of each pixel of said reference image portion;

calculating changes of density value, along said first and second directions, between pixels of said reference image portion which have said predetermined distance therebetween;

using said changes in density value to obtain a histogram of density change along said first and second directions of said reference image portion; and defining a maximum rate-of-change point of each said histogram along said first and second directions, respectively, as characteristic points of the reference image portion;

moving said image portion to be examined relative to said reference image until said characteristic points of said reference image portion and image portion to be examined coincide with each other, to co-center the images;

recognizing said image portions as co-centered when said characteristic points coincide with each other;

comparing said histograms of said image portion and said reference image portion with each other;

recognizing said image portions as matching when said histograms correspond to each other within a predetermined amount; and outputting a verification signal when said histograms correspond to each other within a predetermined amount wherein said obtaining histogram step includes calculating a first histogram of density change in said first direction and a second histogram of density change in said second direction, and wherein said characteristic point of said image includes said maximum or minimum points of said first and second histograms.

\* \* \* \* \*

UNITED STATES PATENT AND TRADEMARK OFFICE
CERTIFICATE OF CORRECTION

PATENT NO.   : 5,610,993
DATED        : Mar. 11, 1997
INVENTOR(S)  : YAMAMOTO

It is certified that error appears in the above-identified patent and that said Letters Patent is hereby corrected as shown below:

ON THE COVER PAGE:
Reads:

[73]    Assignee:   Yozan Inc., Tokyo, Japan

Should Read:

[73]    Assignee:   Yozan Inc., Tokyo Japan
                                Sharp Corporation, Osaka, Japan Signed and Sealed this Twenty-fourth Day of March, 1998

*Attest:*

BRUCE LEHMAN

*Attesting Officer*          *Commissioner of Patents and Trademarks*